United States Patent
Defrize et al.

(10) Patent No.: US 12,310,341 B2
(45) Date of Patent: May 27, 2025

(54) BEETLE POWDER AND METHOD FOR RAISING BEETLES COMPRISING AN ULTRAVIOLET TREATMENT FOR PREPARING SUCH A POWDER

(71) Applicant: NUTRI'EARTH, Lille (FR)

(72) Inventors: Jerémy Defrize, Santes (FR); Thomas Dormigny, Meurchin (FR); Charles-Antoine Destailleur, Emmerin (FR)

(73) Assignee: NUTRI'EARTH, Lille (FR)

( * ) Notice: Subject to any disclaimer, the term of this patent is extended or adjusted under 35 U.S.C. 154(b) by 879 days.

(21) Appl. No.: 17/052,422

(22) PCT Filed: May 22, 2019

(86) PCT No.: PCT/FR2019/051168
§ 371 (c)(1),
(2) Date: Nov. 2, 2020

(87) PCT Pub. No.: WO2019/229332
PCT Pub. Date: Dec. 5, 2019

(65) Prior Publication Data
US 2021/0360946 A1 Nov. 25, 2021

(30) Foreign Application Priority Data
May 28, 2018 (FR) ...................... 1854534

(51) Int. Cl.
*A01K 67/30* (2025.01)
(52) U.S. Cl.
CPC ........ *A01K 67/30* (2025.01); *A01K 2227/706* (2013.01)
(58) Field of Classification Search
CPC .... A23K 10/20; A23K 20/174; A01K 67/033; A01K 2227/706; A01K 67/30; A23L 33/155
See application file for complete search history.

(56) References Cited

U.S. PATENT DOCUMENTS

| | | | |
|---|---|---|---|
| 2017/0042131 A1* | 2/2017 | Unger | A01K 67/033 |
| 2017/0325431 A1* | 11/2017 | Leo | A23K 20/174 |
| 2018/0049414 A1* | 2/2018 | Leo | C11C 1/10 |
| 2018/0049417 A1* | 2/2018 | Leo | A23K 20/174 |
| 2018/0049418 A1* | 2/2018 | Leo | A01K 67/033 |
| 2018/0103679 A1* | 4/2018 | Leo | A01K 67/033 |
| 2019/0085279 A1* | 3/2019 | Leo | A23L 2/56 |
| 2019/0246591 A1* | 8/2019 | Leo | B01D 11/0296 |
| 2021/0137137 A1* | 5/2021 | Leo | B01D 5/006 |

FOREIGN PATENT DOCUMENTS

| | | | | |
|---|---|---|---|---|
| CN | 104905252 A | * | 9/2015 | |
| CN | 108207822 A | * | 6/2018 | ............ A01G 31/00 |
| CN | 108244060 A | * | 7/2018 | ........... A01K 67/033 |
| CN | 108739678 A | * | 11/2018 | ........... A01K 67/033 |
| CN | 108849750 A | * | 11/2018 | ........... A01K 67/033 |
| KR | 200436604 Y1 | * | 9/2007 | |
| KR | 20190066925 A | * | 6/2019 | |
| WO | WO-2022058660 A1 | * | 3/2022 | ........... A01K 1/0151 |

OTHER PUBLICATIONS

CN-104905252-A (Machine Translation from Clarivate) (Year: 2015).*
Mark D. Finke, Gut Loading to Enhance the Nutrient Content of Insects As Food for Reptiles: A Mathematical Approach, Zoo Biology, Wiley InterScience, Sep. 25, 2002, pp. 147-162.
Mark D. Finke et al, Insects as Food for Insectivores, Elsevier Science & Technology, 2013, pp. 583-616.
Aura De Wit, Rearing of Bombyx mori with a vitamin D enriched diet, Thesis, Jun. 2017, pp. 14-28, Almere, Netherlands.
Mark D. Finke, Complete Nutrient Content of Four Species of Commercially Available Feeder Insects Fed Enhanced Diets During Growth, Zoo Biology, Wiley Online Library, Sep. 14, 2015, pp. 554-564.
M.D. Finke, Complete nutrient content of three species of wild caught insects, pallid-winged grasshopper, rhinoceros beetles and white-lined sphinx moth, Journal of Insects as Food and Feed, Jul. 6, 2015, pp. 281-292.
Birgit A. Rumpold et al., Nutritional composition and safety aspects of edible insects, Molecular Nutrition & Food Research, May 2013, pp. 802-823.
Masatoshi Hori et al., Lethal effects of short-wavelength visible light on insects, Scientific Reports, Dec. 9, 2014, pp. 1-6.
Lenka Kourimska et al., Nutritional and sensory quality of edible insects, NFS Journal-Elsevier GmbH on behalf of Society of Nutrition and Food Science, Jul. 12, 2016, pp. 22-26.
Coleoptera, fr.wikipedia.com, Nov. 1, 2019, pp. 1-17.
International Search Report from PCT/FR2019/051168 Sep. 23, 2019, 5 pgs.

* cited by examiner

*Primary Examiner* — Joshua J Michener
*Assistant Examiner* — Aaron M Rodziwicz
(74) *Attorney, Agent, or Firm* — Tutunjian & Bitetto, P.C.

(57) ABSTRACT

A beetle powder including a percentage by weight of vitamin D3 greater than or equal to at least 0.00001% and a percentage by weight of calcium greater than or equal to at least 0.1%, the percentages by weight being given on the total weight of the beetle powder. Additionally, a method for rearing beetles for preparing the beetle powder, which includes a light treatment phase during which a UV source emits ultraviolet rays towards the beetles.

15 Claims, No Drawings

BEETLE POWDER AND METHOD FOR RAISING BEETLES COMPRISING AN ULTRAVIOLET TREATMENT FOR PREPARING SUCH A POWDER

BACKGROUND

The present invention relates to the field of nutrition.

One of the objects of the present invention relates more specifically to the composition of a nutritional powder rich in vitamin D3 and produced from insects and particularly from beetles.

One of the other objects of the present invention also relates to a method for rearing beetles for the preparation of such a composition and the use thereof in human or animal nutrition.

The present invention will thus find numerous applications particularly in the food industry, and particularly for human nutrition, reptile nutrition, or indeed fish farming.

At the present time, more than two thousand edible insect species are recorded worldwide (according to an FAO source).

The use of edible insects as a nutrient source for human or animal nutrition represents an untapped potential which is furthermore increasingly being recognised, particularly in Europe.

Studies have demonstrated that some insect species combine very advantageous nutritional properties in both qualitative and quantitative terms.

Moreover, it is known that insect-based food production has a lower environmental impact (see in particularly the publications *Belluco et al.*, 2013, *Oonincx et al*, 2010 or indeed *Van Huis et al.* 2013).

Studies on the nutritional potential of certain beetle species have been intensified in recent years.

In the species *Tenebrio molitor* or *Alphitobius diaperinus*, the larval stages and the nymph stage are of the greatest interest from a nutritional point of view.

Indeed, these studies demonstrate that the larvae and nymphs of these two species contain a wide diversity of nutrients of interest including proteins (between 50 and 66% of the dry weight), essential fatty acids such as omega-3s of which ALAs, vitamins or indeed minerals.

Among the nutrients of interest present in these beetles, vitamin D3 (or cholecalciferol) which is a form of vitamin D is more specifically found.

Vitamin D3 has important properties.

In humans, vitamin D3 helps maintain normal blood calcium and phosphorus levels absorbed by the intestine.

Vitamin D3 therefore plays a key role in skeletal muscle and bone maintenance. It is used alongside calcium to prevent osteoporosis in elderly subjects.

At the present time, it is known that about 80% of people suffer from vitamin D3 deficiency.

The daily requirements of vitamin D3 are 5 µg for children from 4 years of age to adulthood, but rises to 10 µg in children under 3 years of age, pregnant women, and elderly subjects.

In reptiles, vitamin D3 enables optimal calcium uptake and bone mineralisation.

Conventionally, dietary sources containing vitamin D3 are essentially found in fish particularly via fish oils, fillets or livers.

However, fish represent a declining resource, which is therefore becoming increasingly expensive.

For these reasons, it becomes necessary to find alternative sources of vitamin D3 in keeping with a sustainable and responsible approach.

This vitamin D3 with decisive nutritional properties is therefore among the fat-soluble vitamins that can be found in certain species of beetles such as *Tenebrio molitor* and *Alphitobius diaperinus*.

Producing nutritional powders based on these beetles is therefore known.

The "Klasing et al" study (1999) demonstrates that, in *Tenebrio molitor* larvae, the intake of a dry feed containing 675 IU of vitamin D3 per 1000 grammes of feed for 15 days induced a vitamin D3 concentration of 139 IU.

At the present time, the only known means of increasing the vitamin D3 content is therefore that of adding vitamin D3 supplementation in powder form to the feed of these species.

The Applicant proposes that the vitamin D3 concentrations per 100 grammes of live or dried matter in *Tenebrio molitor* or *Alphitobius diaperinus* fed with vitamin D3 supplementation in powder form remains however low if it is sought to use these species as a nutritional supplement for vitamin D3 in human or animal nutrition.

Such powders obtained with vitamin D3 supplementation when rearing beetles are therefore not economically or nutritionally satisfactory.

SUMMARY OF THE INVENTION

The present invention is intended to improve the current situation described above.

The present invention is more specifically intended to remedy the various drawbacks mentioned above by proposing a solution to significantly increase the vitamin D3 content in live *Tenebrio molitor* or *Alphitobius diaperinus* and/or in the powder obtained after processing without involving increasing addition of vitamin D3 in the insect feed during the larval stage.

The subject matter of the present invention relates according to a first aspect to a beetle powder including a percentage by weight of vitamin D3 greater than or equal to at least 0.00001%, the percentage by weight being given herein on the total weight of beetle powder.

It will be understood that the composition of this powder thus includes, per 100 grammes of beetle powder, at least 10 µgrammes of vitamin D3 and 0.1 grammes of calcium.

Such vitamin D3 contents are of great interest and make it possible to obtain a powder rich in vitamin D3 particularly to meet daily requirements in humans.

Preferably, the beetle powder according to the present invention including a percentage by weight of vitamin D3 greater than or equal to at least 0.000015%, preferentially greater than or equal to at least 0.000025%. Advantageously, the beetle powder according to the present invention includes a percentage by weight of calcium greater than or equal to at least 0.1%, the percentage by weight being given on the total weight of beetle powder.

Advantageously, the powder according to the present invention includes a percentage by weight of fat between 5% and 40%, the percentage by weight being given on the total weight of beetle powder.

Advantageously, the powder according to the present invention has a water activity of less than 0.7.

The water activity conventionally represents the vapour pressure of water of a wet substance divided by the saturating vapour pressure at the same temperature. This parameter expresses the interactions of water with the food matrix.

This water activity is thus considered as one of the main parameters influencing the preservation of foods and pharmaceutical products.

It will be noted herein that such a value less than 0.7 thus enables satisfactory powder preservation.

The subject matter of the present invention relates according to second aspect to a method for rearing beetles for preparing a beetle powder as described above.

According to the present invention, the method includes a light treatment phase during which an ultraviolet source (or UV source) emits ultraviolet rays towards the beetle larvae.

This light treatment while rearing the beetles makes it possible, after processing, to obtain a beetle powder rich in vitamin D3.

Preferably, the UV source is held in position above the beetle larvae.

In a specific embodiment of the present invention, the light treatment phase is applied during the larval stage and/or the nymph stage of the beetles.

The term "larval stage" includes all stages before the nymph stage. The term "nymph stage" for its part corresponds to the intermediate phase between the final larval stage and the adult stage.

Advantageously, the light treatment stage starts between the sixth week and the twelfth week of growth of the larvae, preferably between the ninth and the eleventh week.

Starting the treatment phase during this period has shown advantageous yields.

Advantageously, the light treatment phase has a treatment duration between one and six weeks, preferably between two and four weeks.

Advantageously, the ultraviolet rays emitted by the UV source towards the beetle larvae are:
  UVB type and consist of electromagnetic radiation wherein the wavelength is between 280 nm and 320 nm, and/or
  UVA type and consist of electromagnetic radiation wherein the wavelength is between 320 nm and 400 nm.

It will be noted herein that light emission in the visible range has no impact on vitamin D3 synthesis.

In a specific embodiment of the present invention, which can be combined with one of the preceding modes above, the UV source is positioned, during the light treatment phase, at a defined distance from the beetle larvae between the order of 2 to 250 cm, preferably between 10 and 100 cm, preferentially between 15 and 50 cm.

This distance is relevant and advantageously helps limit the impact on the larvae on the inherent heat supply of the UV source.

In a specific embodiment of the present invention which can be combined with one of the preceding embodiments above, the UV source has a radiation power between 13 and 125 Watts, preferably between 20 and 50 Watts.

This power is relevant and advantageously helps limit the impact on the larvae of the inherent heat supply of the UV source.

In a specific embodiment of the present invention which can be combined with one of the preceding embodiments above, the UV source emits, during the light treatment phase, the ultraviolet rays towards the beetle larvae according to treatment periods between ten hours and twenty-four hours continuously or cumulatively over a twenty-four hour period.

These treatment periods induce greater vitamin D3 synthesis. The larvae are kept in complete darkness when the UV treatment is absent.

This represents a satisfactory yield in vitamin D3 synthesis.

In a specific embodiment of the present invention which can be combined with one of the preceding embodiments above, the beetle larvae are kept in an environment having a substantially constant temperature between 24 and 30° C., preferably between 26 and 28° C. This environment temperature range makes it possible to add a UV source without the additional heat from this UV source impacting the survival of the beetle larvae.

In a specific embodiment of the present invention which can be combined with one of the preceding embodiments above, the beetle larvae are kept in an environment having a substantially constant hygrometry between 45 and 70% relative humidity, preferably between 55 and 65%.

Advantageously, the method according to the present invention includes, prior to the start of the light treatment phase, an initial so-called darkness phase during which, after hatching the beetle larvae, the larvae are kept in darkness between twelve and twenty-two hours per day, preferably between eighteen and twenty hours per day.

Advantageously, the temperature and/or hygrometry of the environment of the beetle larvae is/are controlled such that, between the darkness and light treatment phases, the difference in temperatures is less than or equal to 2° C. and/or the difference in hygrometries is less than or equal to 10% relative humidity.

This controlled management of the ambient parameters makes it possible to obtain a superior yield in vitamin D3 synthesis.

Preferably, the beetle larvae are fed with a diet based on plants and/or vegetables.

Preferably, the beetles are selected among the following species: *Tenebrio molitor*, *Alphitobius diaperinus*.

The subject matter of the present invention relates according to a third aspect to a use of the beetle powder as described above in human or animal nutrition.

Preferably, such a powder is used as a nutritional supplement for example.

Further advantageous uses may be envisaged such as for example reptile or fish feed.

Through the different technical characteristics above, and particularly an ultraviolet-based light treatment in beetle larvae, the present invention makes it possible to obtain a beetle powder containing a percentage of vitamin D3 greater than 0.00001% (400 IU) and at least 0.1% calcium, the percentage being given on 100 grammes of beetle powder, i.e. 10 µgrammes of vitamin D3 per 100 grammes of powder and 0.1 grammes of calcium per 100 grammes of powder.

DETAILED DESCRIPTION

The following examples are given merely by way of illustration of the invention in respect of which they have no limiting nature.

The rearing method that will be described herein is intended to develop a technique to significantly increase the vitamin D3 content in live *Tenebrio molitor* or *Alphitobius diaperinus* and/or in the associated powder obtained after processing without involving increasing addition of vitamin D3 in the insect feed during the larval stage as known in the prior art.

For the purposes of clarity and conciseness, the term beetles hereinafter in the description denotes the following species: *Tenebrio molitor* and/or *Alphitobius diaperinus*.

It is known that it is possible to vary the quantities of nutrients present in beetles according to the stage during growth, the type of feed, the processing method and the quality of the packaging and storage.

The underlying concept of the present invention is therefore that of using a UV treatment on beetles to increase the vitamin D3 content, without vitamin D3 supplementation in the feed.

The rearing method thus comprises several phases which will be described hereinafter in the description.

Initial Phase

The formulation and quantities of feed for the beetle larvae are controlled from hatching to prevent any bias in the trials.

After hatching, the larvae are kept in plastic containers at a temperature between 24 and 30° C., more preferentially between 26 and 28° C. and a hygrometry between 45 and 70% relative humidity, more preferentially between 55 and 65% relative humidity.

Before the light treatment phase that will follow this phase, the larvae are kept in darkness between 12 and 22 hours per day, more preferentially between 18 and 20 h per day.

In each container, the larva density is optimised to obtain a mortality rate close to 0 on the growth cycle between 10 and 16 weeks, more preferentially between 11 and 13 weeks.

The feed supplied to the larvae is 100% plant-based.

The quantities of feed are adapted to the numbers of larvae and to the development stage thereof.

In the example described herein, it is envisaged from the sixth week of growth to give the larvae pre-cleaned vegetables in suitable quantities for the numbers of larvae and the development stage thereof.

Light Treatment or UV Treatment Phase

In the various tests conducted, a light treatment during which a UV source emits UVA and/or UVB towards the beetles is performed during this phase.

The various tests demonstrate that the intensity of the ultraviolet treatment will directly impact the vitamin D3 in the larvae.

This vitamin D3 intensity will depend on several factors: the distance from the UV source, the power of the UV source, the treatment frequency, the treatment duration, and the treatment period.

The distance of the ultraviolet source with respect to the larvae must be positioned between 15 and 50 cm. This distance helping limit the impact on the larvae of the inherent heat supply of the UV source.

The power of the ultraviolet source must be between 20 and 50 Watts. This power helping limit the impact on the larvae of the inherent heat supply of the UV source.

Over a day of treatment including 24 hours, the treatment frequency comprises UV treatment periods between 10 h and 24 h continuously or cumulatively over the 24 h. These treatment periods induce greater vitamin D3 synthesis. The larvae are kept in complete darkness when the UV treatment is absent.

The treatment duration is between 1 and 6 weeks, more preferentially between 2 and 4 weeks. These durations make it possible to obtain appropriate vitamin D3 contents for the use of the powder as a nutritional supplement.

The treatment can start between the 6th week and the 12th week of growth of the larvae, preferably between the 9th and 11th week. This period corresponds to optimal larva sizes.

The emission spectrum of the ultraviolet source comprises electromagnetic radiation with wavelengths between 280 and 400 nm.

Preferably, the temperature and the relative humidity for each of the phases were controlled so that there was not more than 2° C. and 10% RH in difference in particular between the treatments with and without lamps (initial phase and UV treatment phase).

The larvae are then processed as described in the next paragraph.

Processing Phase

Between the 6th and 14th week of growth, more preferentially between the 10th and 13th week of growth, the larvae are sieved to remove excrement.

The sieved larvae are then placed in a plastic container for a fasting period of 24 to 48 hours.

After fasting, the larvae are once again sieved to remove excrement.

The larvae are placed in water between 85° C. and 100° C. to be killed for 1 to 4 minutes.

During this processing, immediately before killing, a stunning step between 0 and 4° C. for several minutes is further envisaged.

After the killing, the larvae are placed at a temperature between 50 and 150° C. for a duration between 1 h 20 and 24 h according to the temperature use. The larvae obtained contain between 2 and 15% water, more preferentially between 3 and 8% water and a water activity less than 0.7

The reduction into powder is then obtained by grinding.

The term powder includes herein any reduction to an element less than 3 mm of the whole insects in the larval or nymph stage thereof or merely of a body part of these insects.

TESTS AND RESULTS

To demonstrate the influence of UVA and UVB on the vitamin D concentration in beetle larvae, several tests were conducted on larvae aged from 6 to 12 weeks and more preferentially aged from 9 to 11 weeks:

"UV+/D3+" Test:

A container containing 500 g of larvae was placed under a UVA-UVB fluorescent lamp 30 cm above the container. The larvae were fed from the hatching thereof with feed supplemented with vitamin D3 (2500 IU/1000 g).

"UV+/D3−" Test:

A container containing 500 g of larvae was placed under a UVA-UVB fluorescent lamp 30 cm above the container. The larvae were fed from the hatching thereof with feed devoid of vitamin D3.

"UV−/D3+" Test:

a container containing 500 g of larvae was placed under a visible-light halogen lamp ("Warm white", 2700K) 30 cm above the container containing no UV emission. The larvae were fed from the hatching thereof with feed supplemented with vitamin D3 (2500 IU/1000 g).

The term visible light denotes electromagnetic radiation wherein the wavelength is between 400 nm and 700 nm.

"Dark Ctrl" Test:

A container containing 500 g was placed in 24 h darkness for a similar period to that of the light treatment tests.

The results of these tests are appended to the present description and show the vitamin D3 content.

The vitamin D3 quantification analyses were carried out by an independent Cofrac-certified laboratory. The quantification is carried out by semi-preparative HPLC followed by reverse-phase HPLC with UV/DAD detector (265 nm).

These results show the influence of UVB on the vitamin D3 concentration. In the "UV+/D3+" and "UV+/D3−" tests conducted herein, it is demonstrated that a UV-based light treatment makes it possible to multiply the vitamin D3 content to 13.

It will be noted that vitamin D3 supplementation during the treatment improves yields. On the other hand, without supplementation, the vitamin D3 content is multiplied by 5, which is very satisfactory in terms of performance.

Indeed, the analyses demonstrate that the concentration changes from 2 µg/100 g to 26 µg/100 g under the effect of a UV treatment during the larval stage.

On the other hand, a light treatment using light from the visible spectrum (400-700 nm) does not give rise to an increase in the vitamin D3 content in larvae.

Therefore, the UV trigger vitamin D3 synthesis even in the absence of supplementation in the feed.

The present invention therefore relates to the method for rearing beetles for preparing a beetle powder as well as the powder obtained from beetles reared according to the rearing method as described above.

It should be observed that this detailed description relates to a specific embodiment example of the present invention, but that this description in no way applies any limiting nature to the subject matter of the invention; on the contrary, it is intended to remove any inaccuracy or any incorrect interpretation of the following claims.

It should also be observed that the reference signs placed between parentheses in the following claims are in no way limiting; these signs are merely intended to improve the intelligibility and comprehension of the following claims as well as the scope of the protection sought.

APPENDIX

| Test | Vitamin D3 concentration (µg/100 g) |
|---|---|
| UV+/D3+ | 10 |
| UV+/D3− | 26 |
| UV−/D3+ | 1.66 |
| Dark Crtl | 2 |

The invention claimed is:

1. A method for rearing beetles for preparing a beetle powder comprising:
   selecting beetle larvae of a beetle species from a group including Tenebrio molitor and Alphilobus diaperinus;
   increasing a nutritional value of the beetle larvae and resulting beetle powder, having a percentage by weight greater than or equal to at least 0.000010% in vitamin D3, by:
      applying a light treatment phase during which a UV source emits ultraviolet rays of UVA type having electromagnetic radiation with wavelength between 320 nm and 400 nm towards beetle larvae;
      limiting a treatment duration of the light treatment phase between one and six weeks; and
      limiting a heat applied on the beetle larvae based on a position of the UV source relative to the beetle larvae and a radiation power, between 13 and 125 Watts, of the UV source.

2. The method according to claim 1, wherein the light treatment phase is applied during a larval stage and/or a nymph stage of the beetles.

3. The method according to claim 2, wherein the light treatment phase starts between a sixth week and a twelfth week of growth of the larvae.

4. The method according to claim 1, further comprising, during the light treatment phase, positioning the UV source at a defined distance from the beetle larvae of the order of 2 to 250 cm.

5. The method according to claim 4, wherein the distance between the UV source and the beetle larvae is between 10 and 100 cm.

6. The method according to claim 4, wherein the distance between the UV source and the beetle larvae is between 15 and 50 cm.

7. The method according to claim 1, wherein the radiation power is between 20 and 50 Watts.

8. The method according to claim 1, wherein during the light treatment phase, the UV source emits the ultraviolet rays towards the beetle larvae according to treatment periods between ten hours and twenty-four hours continuously or cumulatively over a twenty-four hour period.

9. The method according to claim 1, wherein the beetle larvae are kept in an environment having a constant temperature between 24 and 30° C.

10. The method according to claim 1, wherein the beetle larvae are kept in an environment having a constant hygrometry between 45 and 70% relative humidity.

11. The method according to claim 1, further comprising, prior to the light treatment phase, applying an initial darkness phase during which, after hatching the beetle larvae, the larvae are kept in darkness between twelve and twenty-two hours per day.

12. The method according to claim 11, wherein the beetle larvae are kept in an environment having a constant temperature between 24 and 30° C., and having a constant hygrometry between 45 and 70% relative humidity, the method further comprising:
   controlling the temperature and/or hygrometry of the environment of the beetle larvae such that, between the darkness and light treatment phases, a difference in temperatures is less than or equal to 2° C. and/or a difference in hygrometries is less than or equal to 10% relative humidity.

13. The method according to claim 1, further comprising feeding the beetle larvae with a diet based on plants and/or vegetables without vitamin D3 supplementation.

14. The method according to claim 1, further comprising processing the beetle larvae to produce the resulting beetle powder having a percentage by weight greater than or equal to at least 0.000010% in vitamin D3 by:
   warming the beetle larvae in water having a temperature between 85° C. and 100° C.;
   stunning the beetle larvae by placing the beetle larvae at an environment with temperature between 0° C. and 4° C. immediately before killing; and
   grinding the beetle larvae, after a killing process, into the resulting beetle powder.

15. The method according to claim 14, wherein processing the beetle larvae further comprises sieving the beetle larvae before and after a fasting period performed on the beetle larvae to remove excrement.

\* \* \* \* \*